United States Patent
Ottinger et al.

(10) Patent No.: US 11,193,853 B2
(45) Date of Patent: Dec. 7, 2021

(54) REMANUFACTURABLE SENSING ASSEMBLIES AND METHODS OF REMANUFACTURE

(71) Applicant: Cummins Emission Solutions Inc., Columbus, IN (US)

(72) Inventors: Nathan A. Ottinger, Lenoir City, TN (US); Z. Gerald Liu, Madison, WI (US); Rafael Ernesto Vasquez Lombardo, Columbus, IN (US); Krishna Pradeep Chilumukuru, Columbus, IN (US)

(73) Assignee: Cummins Emission Solutions Inc., Columbus, IN (US)

( * ) Notice: Subject to any disclaimer, the term of this patent is extended or adjusted under 35 U.S.C. 154(b) by 156 days.

(21) Appl. No.: 16/750,987

(22) Filed: Jan. 23, 2020

(65) Prior Publication Data

US 2020/0240873 A1    Jul. 30, 2020

Related U.S. Application Data

(60) Provisional application No. 62/797,737, filed on Jan. 28, 2019.

(51) Int. Cl.
*G01M 15/10* (2006.01)
*G01M 15/02* (2006.01)
*F01N 11/00* (2006.01)

(52) U.S. Cl.
CPC ............ *G01M 15/02* (2013.01); *F01N 11/00* (2013.01); *G01M 15/102* (2013.01)

(58) Field of Classification Search
CPC .......................... G01M 15/02; G01M 15/102
See application file for complete search history.

(56) References Cited

U.S. PATENT DOCUMENTS

| | | | | |
|---|---|---|---|---|
| 4,001,758 | A | * | 1/1977 | Esper .................. G01N 27/12 338/34 |
| 4,111,778 | A | * | 9/1978 | Davis ............... G01N 27/4077 204/428 |
| 4,141,813 | A | * | 2/1979 | Kita ................. G01N 27/4078 204/428 |
| 4,214,472 | A | * | 7/1980 | Maxwell ............ G01N 27/12 338/34 |

(Continued)

FOREIGN PATENT DOCUMENTS

EP          1 486 779 B1      12/2004

*Primary Examiner* — Eric S. McCall
(74) *Attorney, Agent, or Firm* — Foley & Lardner LLP (57) ABSTRACT

A sensing assembly comprises a sensor housing having a sensing end and a coupling end opposite the sensing end. A sensing element and a heating element are disposed within the sensor housing. A tip cover and coupling end cover removably coupled to the ends of the sensor housing. The tip cover and coupling end cover are configured to be uncoupled from the sensor housing to enable removal of at least one of the sensing element, the heating element, or an integrated sensing/heating element from the sensor housing, and replacement with at least one of a new sensing element or a new heating element, the tip cover and coupling end cover configured to be recoupled to the sensor housing after at least one of the new sensing element or the new heating element is disposed in the sensor housing.

20 Claims, 5 Drawing Sheets

(56) References Cited

U.S. PATENT DOCUMENTS

| Patent/Pub. No. | | Date | Inventor | Classification |
|---|---|---|---|---|
| 4,272,349 | A * | 6/1981 | Furutani | G01N 27/4077 204/429 |
| 4,327,122 | A * | 4/1982 | Chakupurakal | C04B 41/5122 118/724 |
| 4,347,113 | A * | 8/1982 | Fischer | G01N 27/4075 204/428 |
| 4,362,605 | A * | 12/1982 | Bozon | G01N 27/4077 123/703 |
| 4,377,801 | A * | 3/1983 | Weber | G01N 27/12 338/34 |
| 4,437,971 | A * | 3/1984 | Csanitz | F01N 13/008 204/421 |
| 4,507,192 | A * | 3/1985 | Ebizawa | G01N 27/4077 204/428 |
| 4,560,463 | A * | 12/1985 | Frey | G01N 27/4067 204/424 |
| 4,717,464 | A * | 1/1988 | Oshima | G01N 27/4077 204/427 |
| 4,750,256 | A * | 6/1988 | Wertheimer | G01N 27/4062 29/25.03 |
| 4,786,398 | A * | 11/1988 | Wertheimer | G01N 27/4077 204/427 |
| 4,786,399 | A * | 11/1988 | Wertheimer | G01N 27/4062 204/424 |
| 4,842,713 | A * | 6/1989 | Stahl | G01N 27/4077 204/424 |
| 5,031,445 | A * | 7/1991 | Kato | G01N 27/4077 73/23.31 |
| 5,139,639 | A * | 8/1992 | Holleboom | G01N 27/4062 204/424 |
| 5,246,562 | A * | 9/1993 | Weyl | G01N 27/4078 204/424 |
| 5,421,984 | A * | 6/1995 | Saito | G01N 27/4071 204/424 |
| 5,490,412 | A * | 2/1996 | Duce | G01N 27/4062 73/114.73 |
| 5,723,030 | A * | 3/1998 | Renz | G01N 27/4076 204/424 |
| 5,769,063 | A * | 6/1998 | Mizusawa | F02D 41/1495 123/688 |
| 5,985,118 | A * | 11/1999 | Makino | G01N 27/4074 204/426 |
| 6,182,498 | B1 * | 2/2001 | Mizutani | G01N 27/4077 123/691 |
| 6,397,659 | B1 * | 6/2002 | Mizoguchi | G01N 27/407 73/23.2 |
| 8,696,777 | B1 * | 4/2014 | Patil | F01N 13/10 55/385.3 |
| 2001/0022104 | A1 * | 9/2001 | Hibino | G01N 27/4077 73/31.05 |
| 2001/0035045 | A1 * | 11/2001 | Hibino | G01N 27/407 73/31.05 |
| 2001/0045120 | A1 * | 11/2001 | Friese | G01N 27/4077 73/23.31 |
| 2002/0060152 | A1 * | 5/2002 | Hotta | G01N 27/4077 204/429 |
| 2003/0205466 | A1 * | 11/2003 | Matsuzaki | G01N 27/407 204/424 |
| 2004/0050695 | A1 * | 3/2004 | Haraguchi | G01N 27/419 204/424 |
| 2008/0289460 | A1 * | 11/2008 | Whitehead | B25B 13/06 81/463 |
| 2012/0096839 | A1 * | 4/2012 | Chang | F01N 13/008 60/276 |
| 2017/0160249 | A1 * | 6/2017 | Brosio | F01N 13/008 |
| 2018/0238826 | A1 * | 8/2018 | Ujiyama | F01N 11/007 |

* cited by examiner

REMANUFACTURABLE SENSING ASSEMBLIES AND METHODS OF REMANUFACTURE

CROSS-REFERENCE TO RELATED APPLICATIONS

The present application claims priority to and benefit of U.S. Provisional Application No. 62/797,737, filed Jan. 28, 2019, the entire disclosure of which is hereby incorporated by reference herein.

TECHNICAL FIELD

The present disclosure relates generally to renewable or remanufacturable sensing assemblies associated with aftertreatment systems.

BACKGROUND

Exhaust aftertreatment systems include a plurality of sensing assemblies configured to measure various parameters of an exhaust gas flowing through the aftertreatment system. For example, an exhaust aftertreatment system may include a nitrous oxide ($NO_x$) sensing assembly, an oxygen sensing assembly, a carbon monoxide (CO) sensing assembly, an ammonia sensing assembly, a hydrocarbon sensing assembly, a particulate matter sensing assembly, or any other suitable sensing assembly. Sensing assemblies are generally the highest warranty items in aftertreatment systems, i.e., generally have a higher failure rate relative to other components included in aftertreatment systems resulting in warrant claim by a user for repair or replacement of the failed sensing assembly. Generally, when a sensing assembly of an aftertreatment system malfunctions, the malfunctioning sensing assembly is replaced with a new sensing assembly, which increases maintenance costs.

SUMMARY

Embodiments described herein relate generally to sensing assemblies that are remanufacturable and methods of remanufacturing such sensing assemblies. In particular, sensing assemblies described herein include a plurality of components removably coupled to each other such that a malfunctioning component of the plurality of components can be removed and replaced with a new component, and the sensing assembly reassembled with the new component installed therein so as to remanufacture the sensing assembly.

In some embodiments, a sensing assembly comprises a sensor housing having a sensing end and a coupling end opposite the sensing end; a sensing element disposed within the sensor housing; a heating element disposed within the sensor housing; and a tip cover removably coupled to the sensing end of the sensor housing, wherein the tip cover is configured to be uncoupled from the sensor housing to enable at least one of inspection or removal of at least one of the sensing element or the heating element from the sensor housing through the sensing end, and replacement with at least one of a new sensing element or a new heating element, the tip cover configured to be recoupled to the sensor housing after at least one of the new sensing element or the new heating element is disposed in the sensor housing.

In some embodiments, the sensing element is positioned along a longitudinal axis of the sensing assembly.

In some embodiments, the heating element is positioned circumferentially around the sensing element.

In some embodiments, the sensing element further comprises a support structure defining positioning features configured to receive and secure the sensing element and the heating element within the sensor housing.

In some embodiments, the sensing element and heating element are embedded in the support structure.

In some embodiments, the sensing element further comprises a coupling end cover removably coupled to the coupling end of the sensor housing, the coupling end cover configured to be uncoupled from the sensor housing to enable removal of at least one of the sensing element or the heating element from the sensor housing through the coupling end, and replacement with at least one of a new sensing element or a new heating element, the coupling end cover configured to be recoupled to the sensor housing after at least one of the new sensing element or the new heating element is disposed in the sensor housing.

In some embodiments, the sensing assembly further comprises an electrical coupler removably coupled to the sensing element and the heating element; and electrical leads coupled to the electrical coupler and routed out of the sensor housing through the coupling end.

In some embodiments, the sensing assembly further comprises a compliance member disposed within the coupling end cover, the compliance member defining throughholes therethrough, wherein the electrical leads are routed out of the sensor housing through the corresponding throughholes.

In some embodiments, the sensing assembly further comprises a clamp positioned at an interface of the sensor housing and the coupling end cover and configured to removably secure the coupling end cover to the sensor housing.

In some embodiments, a method comprises receiving a sensing assembly. The sensing assembly comprises a sensor housing having a sensing end and a coupling end opposite the sensing end; a sensing element disposed within the sensor housing; a heating element disposed within the sensor housing; and a tip cover removably coupled to the sensing end of the sensor housing. The method further comprises uncoupling the tip cover from the sensing end; inspecting the sensing and heating element; removing the sensing element and the heating element from the sensor housing; identifying that at least one of the sensing element or the heating element is malfunctioning; replacing the at least one of the malfunctioning sensing element or the heating element with a corresponding new sensing element or new heating element; and recoupling the tip cover to the sensor housing, thereby remanufacturing the sensing assembly.

In some embodiments, the sensing assembly is configured to sense a parameter of an exhaust gas flowing through an aftertreatment system.

In some embodiments, the method further comprises replacing the tip cover with a corresponding new tip cover, wherein the remanufacturing includes installing the new tip cover in the sensing assembly.

In some embodiments, the sensing assembly comprises a coupling end cover removably coupled to the coupling end of the sensor housing, and wherein the disassembling also comprises uncoupling the coupling end cover from the sensor housing, the sensing element and the heating element being removed from the sensor housing through the coupling end, and wherein the method further comprises recoupling the coupling end cover to the sensor housing.

In some embodiments, the sensing assembly comprises a clamp at an interface of the sensor housing and the coupling end cover to secure the coupling end cover to the sensor housing, wherein the disassembling also comprises removing the clamp from the interface.

In some embodiments, a method comprises: receiving a sensing assembly, the sensing assembly comprising: a sensor housing having a sensing end and a coupling end opposite the sensing end, a sensing element disposed within the sensor housing, a heating element disposed within the sensor housing, and a tip cover removably coupled to the sensing end of the sensor housing; visually inspecting the sensing assembly for physical damage; in response to determining that the sensing assembly is not severely damaged, disassembling the sensing assembly; replacing the tip cover of the sensing assembly with a new tip cover; visually inspecting the sensor housing; in response to determining based on the visual inspection that the sensor housing is not damaged, retaining the sensor housing; inspecting the sensing element; in response to determining based on the inspection that the sensing element is not damaged, retaining the sensing element; inspecting the heating element; in response to determining based on the inspection that heating element is not damaged, retaining the heating element; and remanufacturing the sensing assembly.

In some embodiments, the method further comprises: in response to determining based on the visual inspection that the sensor housing is damaged, replacing the sensor housing with a new sensor housing, wherein the new sensor housing is used in the remanufacturing of the sensor assembly.

In some embodiments, the sensor housing being damaged comprises mounting threads of the sensor housing being damaged and/or the sensor housing being bent or corroded.

In some embodiments, the method further comprises: in response to determining based on the inspection that the sensing element is damaged, replacing the sensing element with a new sensing element, wherein the new sensing element is used in remanufacturing of the sensor assembly.

In some embodiments, the method further comprises: in response to determining based on the inspection that the heating element is damaged, replacing the heating element with a new heating element, wherein the new heating element is used in remanufacturing of the sensor assembly.

In some embodiments, the sensing assembly further comprises a support structure for the sensing element, and wherein the method further comprises: inspecting the support structure; and in response to determining based on the inspection that the support structure is damaged, replacing the support structure with a new support structure, wherein the new support structure is used in remanufacturing of the sensor assembly.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION

Embodiments described herein relate generally to sensing assemblies that are remanufacturable and methods of remanufacturing such sensing assemblies. In particular, sensing assemblies described herein include a plurality of components removably coupled to each other such that a malfunctioning component of the plurality of components can be removed and replaced with a new component, and the sensing assembly can be reassembled with the new component installed therein so as to remanufacture the sensing assembly.

Sensing assemblies are generally one of the highest warranty items in exhaust aftertreatment systems, i.e., generally have a higher failure rate relative to other components included in aftertreatment systems resulting in warrant claim by a user for repair or replacement of the failed sensing assembly. Failure of the sensing assembly may include cracking due to water impingement on the sensing assembly, contamination of the sensing assembly (e.g., with particulate matter, inorganic metal particles, etc.), failure of a heating element of the sensing assembly, short circuit, etc. Currently, sensing assemblies used in exhaust gas aftertreatment systems are replaced with new sensing assemblies when they malfunction. Malfunction of a sensing assembly may be due to only one component of the sensing assembly malfunctioning, but the entire sensing assembly is typically replaced. This increases maintenance costs. Furthermore, new regulations, aim to double warranty durations of sensing assemblies that will further increase warranty costs as the manufacturers will be responsible for replacing sensing assemblies for the longer warranty duration.

Various embodiments of sensing assemblies and methods of remanufacturing sensing assemblies described herein may provide one or more benefits including, for example: (1) identifying one or more component of a sensing assembly that has malfunctioned and remanufacturing the sensing assembly by replacing the malfunctioning component with a new replacement component; (2) providing sensing assemblies that include a plurality of components removably coupled to each other allowing facile replacement of the malfunctioning component; and (3) reducing maintenance cost by remanufacturing and reusing a sensing assembly instead of replacing the sensing assembly with a new sensing assembly.

While systems and methods are described herein with respect to sensing assemblies for use in aftertreatment systems, it should be appreciated that the concepts described herein are equally applicable to any other sensing assembly used in any other system including but not limited to fuel sensing assemblies, water sensing assemblies, biological sensing assemblies, environmental sensing assemblies, or any other sensing assembly.

Figure 1:
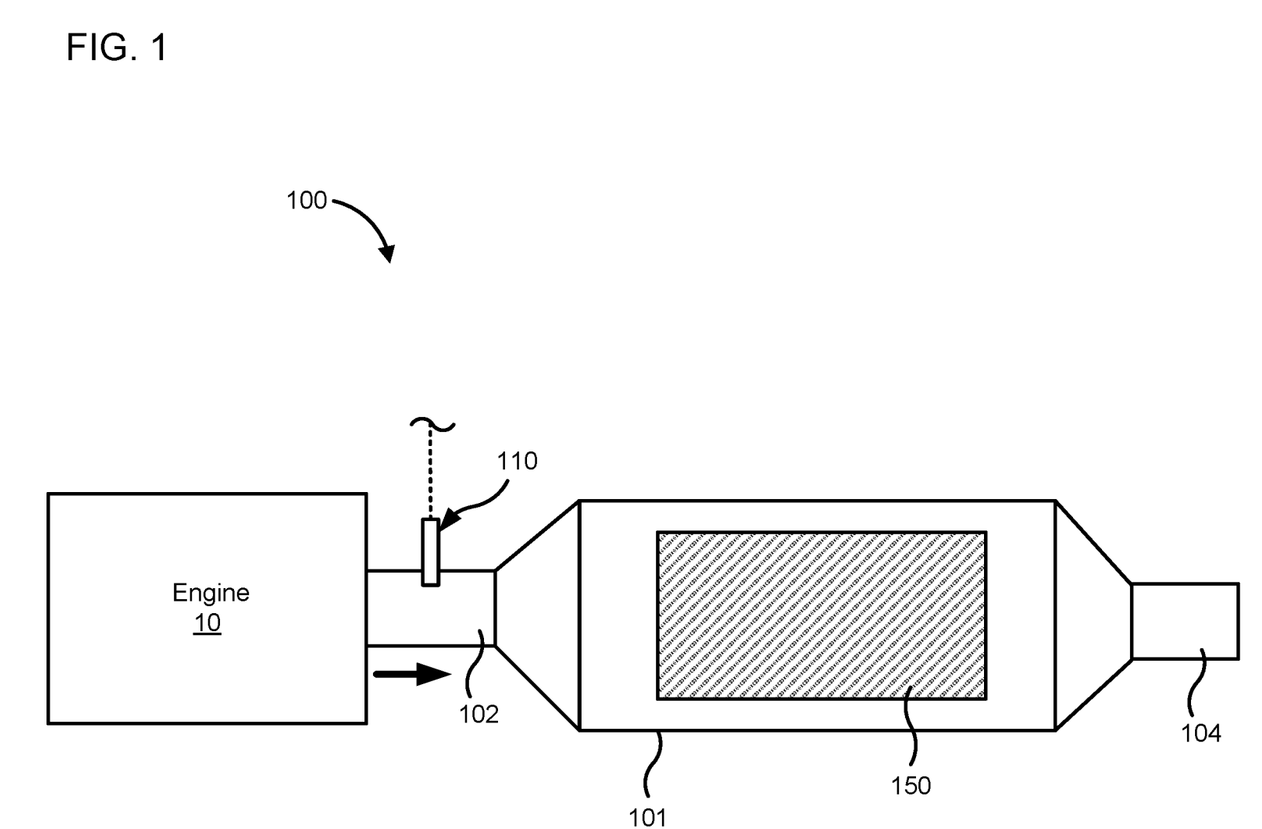
FIG. 1 is a schematic illustration of an aftertreatment system, according to an embodiment.

FIG. 1 is a schematic illustration of an aftertreatment system 100, according to an embodiment. The aftertreatment system 100 may be coupled to an engine 10 (e.g., a diesel engine, a gasoline engine, a natural gas engine, a biodiesel engine, a dual fuel engine, an alcohol engine, an E85 or any other suitable internal combustion engine) and configured to receive an exhaust gas (e.g., a diesel exhaust gas) therefrom. The aftertreatment system 100 is configured to decompose constituents of the exhaust gas such as, for example, $NO_x$ gases (e.g., $NO$, $NO_2$, $N_2O$, $NO_3$, etc.), $CO$, etc. The aftertreatment system 100 may include a housing 101 having an aftertreatment component 150 disposed therein, and a sensing assembly 110.

The housing 101 may be formed from a rigid, heat-resistant and corrosion-resistant material, for example stainless steel, iron, aluminum, metals, ceramics, or any other suitable material. The housing 101 may have any suitable cross-section, for example circular, square, rectangular, oval, elliptical, polygonal, or any other suitable shape.

The aftertreatment component 150 is disposed in an internal volume defined by the housing 101. In some embodiments, the aftertreatment component 150 may include a catalyst configured to decompose constituents of the exhaust gas. In particular embodiments, the aftertreatment component 150 may include a SCR system (e.g., in embodiments in which the exhaust gas includes a diesel exhaust gas), and the catalyst may include a SCR catalyst configured to decompose $NO_x$ gases included in the exhaust gas. Any suitable catalyst can be used such as, for example, rhodium, cerium, iron, manganese, copper, vanadium based catalyst, any other suitable catalyst, or a combination thereof. The SCR catalyst can be disposed on a suitable substrate such as, for example, a ceramic (e.g., cordierite) or metallic (e.g., kanthal) monolith core which can, for example, define a honeycomb structure. A washcoat can also be used as a carrier material for the SCR catalyst. Such washcoat materials may comprise, for example, aluminum oxide, titanium dioxide, silicon dioxide, any other suitable washcoat material, or a combination thereof. The exhaust gas (e.g., diesel exhaust gas) can flow over and/or around the SCR catalyst such that any $NO_x$ gases included in the exhaust gas are further reduced to yield an exhaust gas that is substantially free of $NO_x$ gases.

In some embodiments, the aftertreatment component 150 may include a selective catalytic reduction filter (SCRF) system, or any other aftertreatment component configured to decompose constituents of the exhaust gas (e.g., $NO_x$ gases such as nitrous oxide, nitric oxide, nitrogen dioxide, etc.), flowing through the aftertreatment system 100 in the presence of a reductant, as described herein. In other embodiments, the aftertreatment component 150 may include a three-way catalyst (e.g., in embodiments in which the exhaust gas includes a gasoline exhaust gas).

While shown as including the aftertreatment component 150, in other implementations, the aftertreatment system 100 may include various other aftertreatment components positioned upstream or downstream of the aftertreatment component 150. For example, in embodiments in which the aftertreatment component 150 includes an SCR catalyst, the aftertreatment component 150 may include an ammonia oxidation ($AMO_x$) catalyst to decompose an unreacted ammonia in the exhaust gas to reduce ammonia slip, disposed downstream of the aftertreatment component 150. In other embodiments, the aftertreatment system 100 may also include one or more filters (e.g., a diesel particulate filter), oxidation catalysts (e.g., a carbon monoxide and/or hydrocarbon oxidation catalyst), mixers (e.g., configured to facilitate mixing of a reductant with the exhaust gas), baffle plates, and/or any other suitable aftertreatment component.

An inlet conduit 102 is coupled to an inlet of the housing 101 and structured to receive exhaust gas from the engine 10 and communicate the exhaust gas to an internal volume defined by the housing 101. Furthermore, an outlet conduit 104 may be coupled to an outlet of the housing 101 and structured to expel treated exhaust gas into the environment. A sensing assembly 110 is disposed in the inlet conduit 102. In some embodiments, the sensing assembly 110 may be a $NO_x$ sensing assembly configured to measure an amount of $NO_x$ in the exhaust gas entering the aftertreatment system 100. While shown as being disposed in the inlet conduit 102, in other embodiments, the sensing assembly 110 may be disposed in any other portion of the aftertreatment system 100, or the aftertreatment system 100 may include a plurality of sensing assemblies disposed at various location of the aftertreatment system 100.

For example, in some embodiments, the sensing assembly 110 may be a $NO_x$ or ammonia sensing assembly disposed in the outlet conduit 104 and configured to measure an amount of $NO_x$ or ammonia in the exhaust gas being expelled from the aftertreatment system 100. In other embodiments, the sensing assembly 110 may be an oxygen sensing assembly configured to measure an amount of oxygen in the exhaust gas. In other embodiments, the sensing assembly 110 may be a carbon monoxide sensing assembly, a hydrocarbon sensing assembly, a temperature sensing assembly, a particulate matter sensing assembly or any other suitable sensing assembly.

The aftertreatment system 100 may include other components to facilitate decomposition of components of the exhaust gas not shown in FIG. 1. Such components may include a reductant tank (e.g., configured to store a reductant such as an aqueous urea solution or a diesel exhaust fluid), a reductant insertion assembly and/or a controller configured to control operations of the aftertreatment system 100.

The sensing assembly 110 includes a plurality of components removably coupled to each other. If the sensing assembly 110 malfunctions due to malfunctioning of one or more components included in the sensing assembly 110, instead of having to replace the entire sensing assembly 110, as is the case with conventional sensing assemblies, only the malfunctioning components are replaced with new components.

Figure 2A:
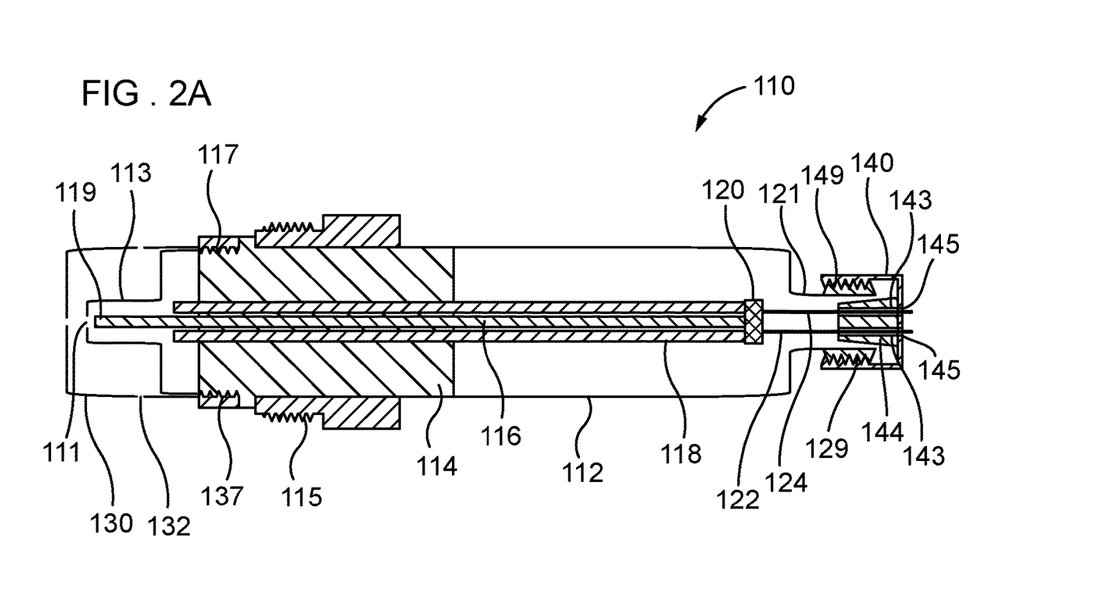
FIG. 2A is a side cross-section view of a sensing assembly, according to an embodiment.

FIG. 2A is a side cross-section view of the sensing assembly 110, according to a particular embodiment. The sensing assembly 110 includes a sensor housing 112 defining an internal volume within which a sensing element 116 and a heating element 118 is disposed. In other embodiments, the heating element 118 may be excluded. The sensor housing 112 may be formed from a heat resistant material, for example, metal or ceramics. Mounting threads 115 are defined on an outer surface of the sensor housing 112 and are configured to engage corresponding threads defined in the housing 101 of the aftertreatment system 100 so as to mount the sensing assembly 110 thereon. In other embodiments, any other suitable coupling elements may be provided on the sensor housing 112 instead or in addition to the mounting threads 115. Such elements may include, for example, coupling pins, snap-fit features, friction fit features or any other suitable coupling features.

A support structure 114 is disposed within the sensor housing 112. The support structure 114 may include a metallic or ceramic element that includes slots, openings or other positioning features shaped and sized to receive and secure the sensing element 116 and the heating element 118 within the sensor housing 112. The support structure 114 may be formed from a heat resistant material, for example, metals or ceramics. In some embodiments, the sensing element 116 and the heating element 118 may be integrated into a single structure or element, for example, by embedding into the support structure 114 (e.g., a ceramic plate).

As shown in FIG. 2A, the sensing element 116 is removably disposed along a longitudinal axis of the sensor housing 112, and secured therewithin via the support structure 114. The sensing element 116 includes a sensing tip 119 extending into a sensing end 113 of the sensor housing 112. A sensing end opening 111 is defined in the sensing end 113 to allow a portion of the exhaust gas to enter and contact the sensing tip 119 of the sensing element 116 such that the sensing element 116 may determine a quantity of a constituent (e.g., NOR, oxygen, CO, ammonia, hydrocarbons, particulate matter, etc.) of the exhaust gas. The heating element 118 may include heating element plates disposed on either side of the sensing element 116. In other embodiments, the heating element 118 may surround the sensing element 116.

A tip cover 130 is coupled to the sensor housing 112 at the sensing end 113. The tip cover 130 may be formed from any suitable heat resistant material, for example, metals or ceramics. The tip cover 130 surrounds the sensing end 113 and protects the sensing end 113, for example, from liquid water directly impinging thereon, which may crack or damage the sensing end 113 or the sensing tip 119. A plurality of tip cover openings 132 are defined in the tip cover 130 and configured to allow the portion of the exhaust gas to enter the tip cover 130 and therefrom through the sensing end opening 111 and contact the sensing tip 119. Sensing end threads 117 are provided on an outer surface of the sensor housing 112 at the sensing end 113. Tip cover threads 137 are provided on an inner surface of the tip cover 130 and configured to mate with the sensing end threads 117 for coupling the tip cover 130 to the sensor housing 112.

An electrical coupler 120 is removably coupled to the sensing element 116 and the heating element 118. Electrical leads 122 and 124 are coupled to the electrical coupler 120 and configured to provide electrical communication between the sensing element 116 and the heating element 118, and a controller (not shown), for example, an electronic control unit. The electrical leads 122 and 124 are routed out of a coupling end 121 of the sensor housing 112, which is opposite the sensing end 113. A coupling end cover 140 is coupled to the coupling end 121 of the sensor housing 112 via coupling end cover threads 149 that engage coupling end threads 129 provided at the coupling end 121 of the sensor housing 112 and removably couple the coupling end cover 140 to the sensor housing 112. In some embodiments, the coupling end cover 140 may include a removable nut.

A compliance member 144 is positioned within the coupling end cover 140 and may include, for example, a rubber or foam member. The compliance member 144 may be tapered radially inwards towards the coupling end 121. The compliance member 144 may define throughholes 143 therethrough. The electrical leads 122 and 124 may be routed through the throughholes 143 out of the sensor housing 112 and through corresponding openings 145 defined in coupling end cover 140. In some embodiments, if the sensing element 116 or the heating element 118 malfunctions, the tip cover 130 may be uncoupled from the sensor housing 112, to allow removal of the sensor element 116 and/or the heating element 118 from the sensor housing 112 through a corresponding sensing end of the sensor housing 112 where the tip cover 130 is located, and replacement with a new sensing and/or heating element 116, 118, thereby remanufacturing the sensing assembly 110. The tip cover 130 may be cleaned and recoupled to the sensor housing 112, or a new tip cover 130 may be coupled to the sensor housing 112. In other embodiments, the coupling end cover 140 may be uncoupled from the coupling end 121 of the sensor housing 112 to allow the sensing element 116 and/or the heating element 118 to be removed from the sensor housing 112 through the corresponding coupling end of the sensor housing 112 opposite the sensing end, and be replaced with a new sensing element 116 and/or the heating element 118. The coupling end cover 140 is then recoupled to the sensor housing 112.

Figure 2B:
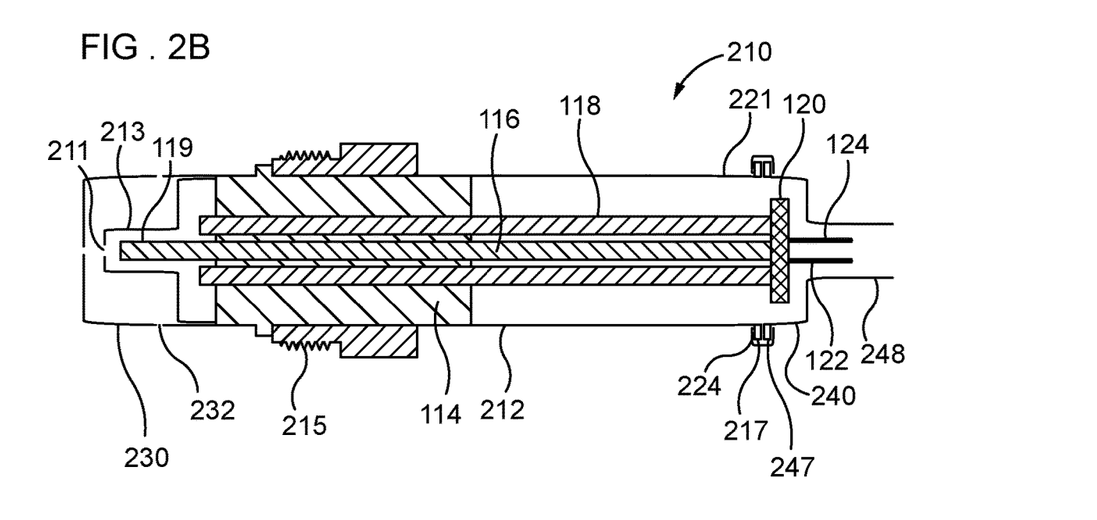
FIG. 2B is a side cross-section view of a sensing assembly, according to another embodiment.

FIG. 2B is a side cross-section view of a sensing assembly 210, according to another embodiment. The sensing assembly 210 includes a sensor housing 212 defining an internal volume within which the sensing element 116 and heating element 118 are disposed. The sensing element 116 and the heating element 118 are secured within the support structure 114, as previously described herein with respect to the sensing assembly 110. The sensor housing 212 may be formed from a heat resistant material, for example, metal or ceramics. Mounting threads 215 are defined on an outer surface of the sensor housing 212 and are configured to engage corresponding threads defined in the housing 101 of the aftertreatment system 100 so as to mount the sensing assembly 210 thereon. In other embodiments, any other suitable coupling elements may be provided on the sensor housing 212 instead or in addition to the mounting threads 215. Such elements may include, for example, coupling pins, snap-fit features, friction fit features or any other suitable coupling features.

The sensing tip 119 of the sensing element 116 extends into a sensing end 213 of the sensor housing 212. A sensing end opening 211 is defined in the sensing end 213 to allow a portion of the exhaust gas to enter and contact the sensing tip 119 of the sensing element 116 such that the sensing element 116 may determine a quantity of a constituent (e.g., NOR, oxygen, CO, ammonia, hydrocarbons, particulate matter, etc.) of the exhaust gas.

A tip cover 230 is coupled to the sensor housing 212 at the sensing end 213. The tip cover 230 may be formed from any suitable heat resistant material, for example, metals or ceramics. The tip cover 230 surrounds the sensing end 213 and protects the sensing end 213, for example, from liquid water directly impinging thereon, which may crack or damage the sensing end 213 or the sensing tip 219. A plurality of tip cover openings 232 are defined in the tip cover 230 and configured to allow the portion of the exhaust gas to enter the tip cover 230 and therefrom through the sensing end opening 211 and contact the sensing tip 219. Different from the tip cover 130, the tip cover 230 is removably coupled to the sensor housing 212 using coupling elements other than threads, for example, friction fit, snap-fit, pins or any other suitable coupling element. In other embodiments, the sensing assembly 210 may include the tip cover 130.

The electrical coupler 120 is removably coupled to the sensing element 116 and the heating element 118. Electrical leads 122 and 124 are coupled to the electrical coupler 120 and configured to provide electrical communication between the sensing element 116 and the heating element 118, and a controller (not shown), for example, an electronic control unit, as previously described herein. The electrical leads 122 and 124 are routed out of a coupling end 221 of the sensor housing 212, which is located opposite the sensing end 213. A coupling end cover 240 is coupled to the coupling end 221 of the sensor housing 212. A coupling end projection 217 protrudes radially outwards from the sensor housing 212 at the coupling end 221 proximate to the coupling end cover 240. Furthermore, a coupling end cover projection 247 protrudes radially outwards from the coupling end cover 240 proximate to the coupling end projection 217.

A clamp 224 is positioned around the projections 217, 247 and removably couples the sensor housing 212 to the coupling end cover 240. For example, the clamp 224 may include a band clamp including a lead screw, or a Marman clamp etc. The clamp 224 may be positioned around the sensor housing 212 and the coupling end cover 240 at the interface thereof, and the lead screw is tightened to secure the clamp 224 to the sensor housing 212 and the coupling end cover 240 at the interface, thereby removably coupling the sensor housing 212 to the coupling end cover 240.

The coupling end cover 240 defines a conduit 248 for routing the electrical leads 122, 124 out of the coupling end cover 240. If the sensing element 116 and/or the heating element 118, malfunctions, the clamp 224 may be removed and the coupling end cover 240 uncoupled from the sensor housing 212 to allow removal of the malfunctioning sensing element 116 and/or the heating element 118 (e.g., individually if the sensing and heating elements 116, 118 are separate from each other or together if the sensing and heating elements 116, 118 are integrated into a single element) from the sensor housing 212 and replacement with a new sensing element and/or heating element.

Figure 3:
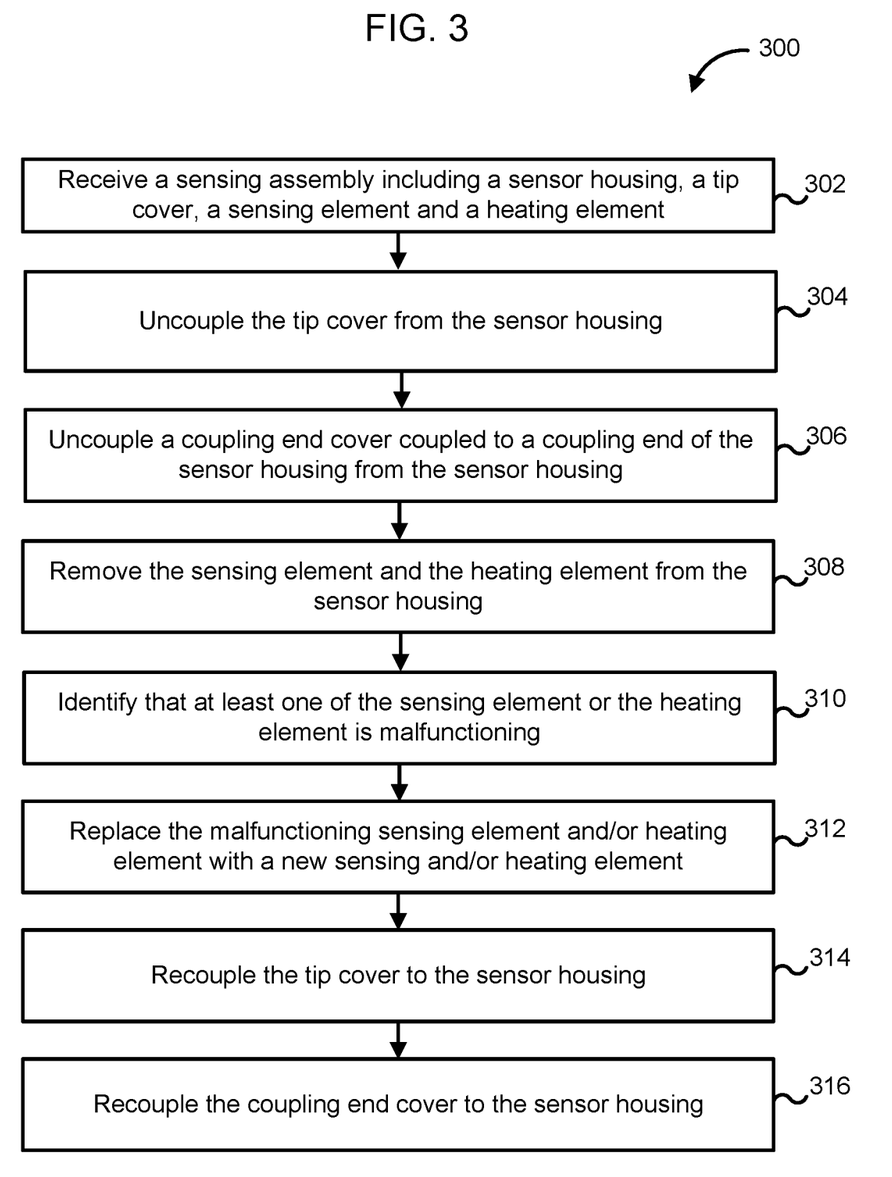
FIG. 3 is a schematic block diagram of a method for remanufacturing a sensing assembly, according to an embodiment.

FIG. 3 is a schematic flow diagram of an example method 300 for remanufacturing a sensing assembly (e.g., the sensing assembly 110, 210), according to an embodiment. The method 300 includes receiving a sensing assembly, at 302. The sensing assembly includes a sensor housing (e.g., the sensor housing 112, 212) having a sensing end and a coupling end opposite the sensing end, a sensing element (e.g., the sensing element 116) and heating element (e.g., the heating element 118) disposed in the sensor housing, and a tip cover (e.g., the tip cover 130, 230) removably coupled to a sensing end of the sensor housing. In some embodiments, the sensing assembly may also include a coupling end cover (e.g., the coupling end cover 140, 240) removably coupled to the coupling end of the sensor housing. For example, the sensing assembly 110, 210 or any other sensing assembly that includes a plurality of components removably coupled to each other may be received at a remanufacturing facility. The sensing assembly 110, 210 may be malfunctioning, for example, due to malfunction of one or more components of the sensing assembly 110, 210 after being used in an aftertreatment system (e.g., the aftertreatment system 100).

At 304, the tip cover is uncoupled from the sensor housing. In some embodiments, the coupling end cover is also uncoupled from the sensor housing, at 306. For example, the tip cover 130, 230 and the coupling end cover 140, 240 are uncoupled from the sensing assembly 110, 210. For example, the coupling end cover (e.g., the coupling end cover 140) may be screwed on to the coupling end of the sensor housing via mating threads, and is uncoupled from the sensor housing by unscrewing the coupling end cover from the sensor housing. In other embodiments, the coupling end cover (e.g., the coupling end cover 240) is removably coupled to the sensor housing via a clamp (e.g., the clamp 224), and is uncoupled from the sensor housing by uncoupling and removing the clamp.

At 308, the sensing element and the heating element are inspected (e.g., visually or using inspection equipment such as electronic testing equipment). At 310, the sensing element (e.g., the sensing element 116) and the heating element (e.g., the heating element 118) are removed from the sensor housing (e.g., the sensor housing 112, 212).

The method 300 further includes identifying that the sensing element and/or the heating element is malfunctioning, at 312. At 314, the malfunctioning sensing element and/or heating element is replaced with a corresponding new sensing element and/or heating element. For example, the tip cover 130, 230 and the sensing end 113, 213 may be visually inspected to determine if the sensing end opening 111 and/or the sensing cover opening 111 are clogged, or whether the tip cover 130, 230 and/or the sensor housing 112, 212 is damaged. If the tip cover 130, 230 and the sensor housing 112, 212 are damaged beyond repair, they may be replaced with a new tip cover and sensor housing. Otherwise, the tip cover 130, 230 and the sensor housing 112, 212 may be cleaned (e.g., with solvents, soap, water, etc.) and used in the remanufactured sensing assembly.

The sensing element 116 and/or the heating element 116 and the electrical coupler 120 may be visually inspected as well as inspected using electrical testing instrumentation (e.g., voltmeter, galvanostat, etc.) to determine if the sensing element 116, the heating element 118 and the electrical coupler 120 are working properly or have malfunctioned. If any of these components are malfunctioning, they are replaced with corresponding new components. Otherwise, the sensing element 116, the heating element 118 and the electrical coupler 120 are cleaned and reused in the sensing assembly 110, 210.

At 316, the sensing assembly is remanufactured by recoupling the tip cover to the sensor housing with the corresponding sensing element and/or heating element (e.g., new or cleaned and reused sensing element and/or heating element) installed in the sensor housing. Furthermore, the coupling end cover may be recoupled to the sensor housing, at 318. In other words, the sensing assembly is reassembled with the components that are working properly and any new components that replace the malfunctioning components. In this manner, the sensing assembly is remanufactured which provide significant cost savings relative to replacing the sensing assembly with a new sensing assembly. In some embodiments, the sensing assembly may also be tested after remanufacturing. For example, sensing performance, noise characteristics, and/or other parameters of the sensing assembly may be tested after remanufacturing using appropriate electrical testing equipment.

Figure 4A:
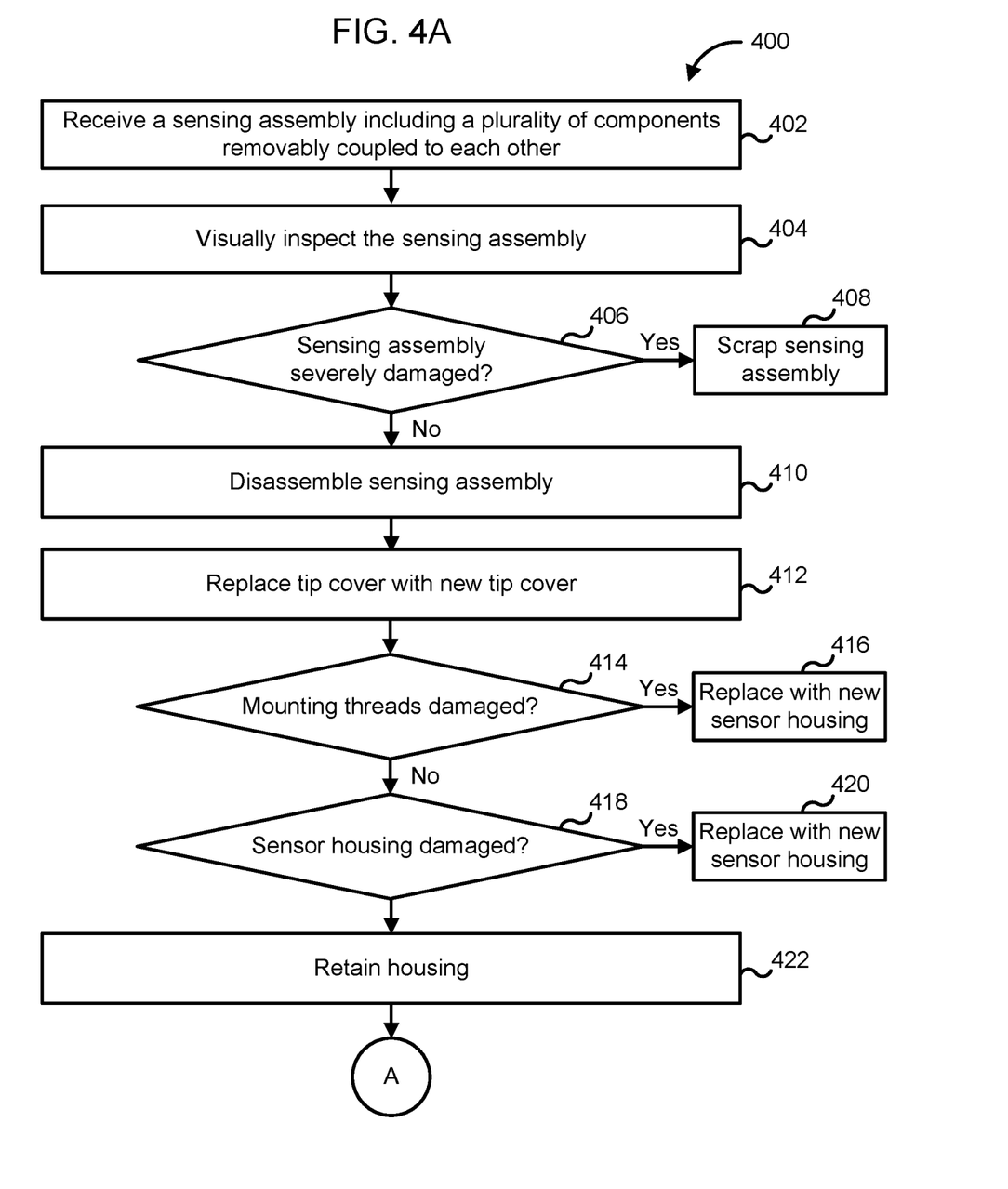
FIGS. 4A-4B are schematic block diagrams of a method for remanufacturing a sensing assembly, according to another embodiment.
Figure 4B:
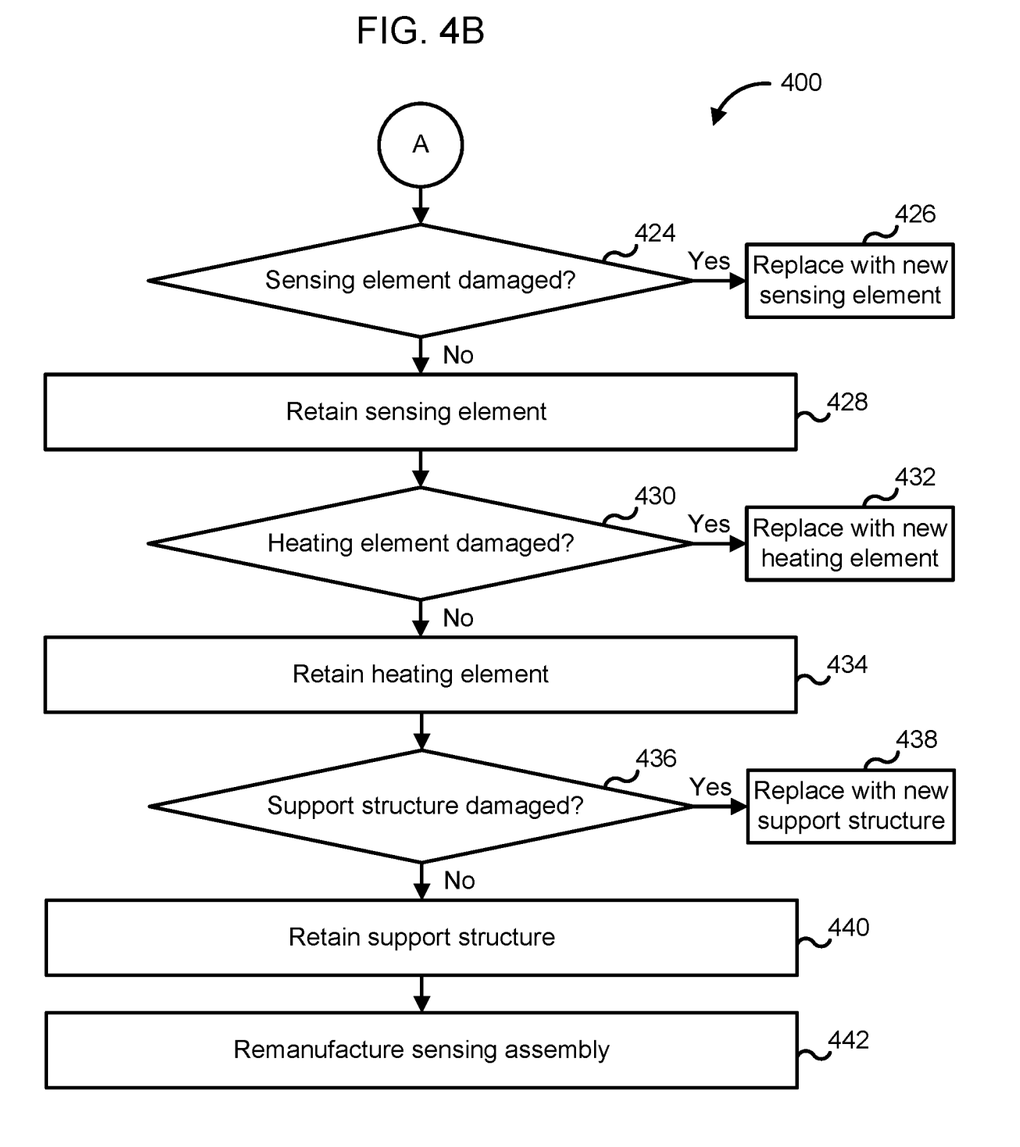

FIGS. 4A-4B are schematic flow diagrams of another method 400 for remanufacturing a sensing assembly (e.g., the sensing assembly 110, 210), according to another embodiment. The method 400 includes receiving a sensing assembly including a plurality of components removably coupled to each other, at 402. For example, the sensing assembly 110, 210 may malfunction after being used in an aftertreatment system (e.g., the aftertreatment system 100)

and the malfunctioning sensing assembly 110, 210 is received at a remanufacturing facility.

At 404, the sensing assembly is visually inspected. For example, a repair person may visually inspect the sensing assembly 110, 210 for physical damage. At 406, the method 400 includes determining whether the sensing assembly is severely damaged. For example, the sensing assembly 110, 210 is visually inspected for cracks, corrosion, crush or bend damage. If the sensing assembly is severely damaged (406:YES), for example, crushed, bent or broken into pieces, the sensing assembly is scrapped, at 408. In such instances, a new sensing assembly is installed in the aftertreatment system.

If the sensing assembly is not severely damaged, at 406 (406:NO), the sensing assembly is disassembled, at 410. For example, the tip cover 130, 230 and the coupling end cover 140, 240 are uncoupled from the sensing assembly 110, 210 and the sensing element 116 and the heating element 118 removed from the sensor housing 112, 212.

At 412, a tip cover of the sensing assembly is replaced with a new tip cover. For example, the tip cover 130, 230 is removed from the sensor housing 112, 212 and replaced with a corresponding new tip cover regardless of whether the tip cover 130, 230 is damaged or is in relatively good shape.

At 414, the method 400 includes determining whether mounting threads of the sensor housing are damaged. For example, the repair person may visually inspect the mounting threads to determine if the mounting threads 115, 215 are damaged, for example, have severe thread wear or corrosion. If the mounting threads 115, 215 are damaged (414:YES), the sensor housing 112, 212 is replaced with a new sensor housing, at 416.

If the mounting threads are not damaged (414:NO), the method 400 includes determining if the sensor housing is damaged, at 418. For example, the repair person may determine if the sensor housing 112, 212 is cracked, bent or corroded. If the sensor housing 112, 212 is damaged beyond repair (418:YES), the sensor housing 112, 212 is replaced with a new sensor housing, at 420. However, if the sensor housing 112 is not damaged (418:NO), the sensor housing 112, 212 is retained. The sensor housing 112, 212 may be cleaned, for example using an air blower, solvents, detergents, etc.

At 424, the method 400 includes determining whether the sensing element is damaged. For example, the repair person may visually inspect the sensing element 116 and/or test the sensing element 116 using electrical testing equipment. If the sensing element 116 is determined to be damaged (424:YES), the sensing element 116 is replaced with a new sensing element, at 426. However, if the sensing element 116 is not damaged (424:NO) and is working properly, the sensing element is retained, at 428. The sensing element 116 may be cleaned and prepared for remanufacturing.

At 430, the method 400 includes determining whether the heating element is damaged. For example, the repair person may visually inspect the heating element 118 or test the heating element 118 using electrical testing equipment. If the heating element 118 is determined to be damaged (430:YES), the heating element is replaced with a new heating element, at 432. However, if the heating element 118 is not damaged (430:NO) and is working properly, the heating element is retained, at 434. The heating element 118 may be cleaned and prepared for remanufacturing. In some embodiments, the sensing element and the heating element may be integrated into a single element, as previously described herein. In such embodiments, the single element including the sensing and heating assemblies is removed, inspected, either repositioned in the sensor housing or replaced with a new element to remanufacture the sensing assembly.

In some embodiments, the method 400 also includes determining if a support structure of the sensing element is damaged, at 436. For example, the repair person may visually inspect the support structure 114 to determine if the support structure 114 is damaged. If the support structure 114 is damaged (436:YES), the support structure is replaced with a new support structure, at 438. If the support structure 114 is undamaged (436:NO), the support structure is retained, at 440. The support structure 114 may be cleaned and prepared for remanufacturing.

At 442, the sensing assembly is remanufactured. For example, the sensing assembly 110, 210 is reassembled using the new components that replaced the malfunctioning components, or the retained components, therefore remanufacturing the sensing assembly 110, 210. The remanufactured sensing assembly 110, 210 may be tested before being installed in an aftertreatment system (e.g., the aftertreatment system 100). In some embodiments, the remanufacturing may also include operations to improve aesthetics of the reassembled sensing assembly including, but not limited to buffing, painting, polishing, etc.

It should be noted that the term "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Additionally, it should be understood that features from one embodiment disclosed herein may be combined with features of other embodiments disclosed herein as one of ordinary skill in the art would understand. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A sensing assembly, comprising:
a sensor housing having a sensing end and a coupling end opposite the sensing end;
a sensing element disposed within the sensor housing;
a heating element disposed within the sensor housing; and
a tip cover removably coupled to the sensing end of the sensor housing,
wherein the tip cover is configured to be uncoupled from the sensor housing to enable at least one of inspection or removal of at least one of the sensing element or the heating element from the sensor housing through the sensing end, and replacement with at least one of a new sensing element or a new heating element, the tip cover configured to be recoupled to the sensor housing after at least one of the new sensing element or the new heating element is disposed in the sensor housing.

2. The sensing assembly of claim 1, wherein the sensing element is positioned along a longitudinal axis of the sensing assembly.

3. The sensing assembly of claim 2, wherein the heating element is positioned circumferentially around the sensing element.

4. The sensing assembly of claim 1, further comprising a support structure defining positioning features configured to receive and secure the sensing element and the heating element within the sensor housing.

5. The sensing assembly of claim 4, wherein the sensing element and heating element are embedded in the support structure.

6. The sensing assembly of claim 1, further comprising a coupling end cover removably coupled to the coupling end of the sensor housing, the coupling end cover configured to be uncoupled from the sensor housing to enable removal of at least one of the sensing element or the heating element from the sensor housing through the coupling end, and replacement with at least one of a new sensing element or a new heating element, the coupling end cover configured to be recoupled to the sensor housing after at least one of the new sensing element or the new heating element is disposed in the sensor housing.

7. The sensing assembly of claim 6, further comprising:
an electrical coupler removably coupled to the sensing element and the heating element; and
electrical leads coupled to the electrical coupler and routed out of the sensor housing through the coupling end.

8. The sensing assembly of claim 7, further comprising a compliance member disposed within the coupling end cover, the compliance member defining throughholes therethrough, wherein the electrical leads are routed out of the sensor housing through the corresponding throughholes.

9. The sensing assembly of claim 7, further comprising a clamp positioned at an interface of the sensor housing and the coupling end cover and configured to removably secure the coupling end cover to the sensor housing.

10. A method, comprising:
receiving a sensing assembly, the sensing assembly comprising:
a sensor housing having a sensing end and a coupling end opposite the sensing end,
a sensing element disposed within the sensor housing,
a heating element disposed within the sensor housing, and
a tip cover removably coupled to the sensing end of the sensor housing;
uncoupling the tip cover from the sensing end;
inspecting the sensing element and the heating element;
removing the sensing element and the heating element from the sensor housing;
identifying that at least one of the sensing element or the heating element is malfunctioning;
replacing the at least one of the malfunctioning sensing element or the heating element with a corresponding new sensing element or new heating element; and
recoupling the tip cover to the sensor housing, thereby remanufacturing the sensing assembly.

11. The method of claim 10, wherein the sensing assembly is configured to sense a parameter of an exhaust gas flowing through an aftertreatment system.

12. The method of claim 11, further comprising replacing the tip cover with a corresponding new tip cover, wherein the remanufacturing includes installing the new tip cover in the sensing assembly.

13. The method of claim 11, wherein the sensing assembly comprises a coupling end cover removably coupled to the coupling end of the sensor housing, wherein the disassembling also comprises uncoupling the coupling end cover from the sensor housing, the sensing element and the heating element being removed from the sensor housing through the coupling end, and wherein the method further comprises recoupling the coupling end cover to the sensor housing.

14. The method of claim 13, wherein the sensing assembly further comprises a clamp at an interface of the sensor housing and the coupling end cover to secure the coupling end cover to the sensor housing, wherein the disassembling also comprises removing the clamp from the interface.

15. A method, comprising:
receiving a sensing assembly, the sensing assembly comprising:
a sensor housing having a sensing end and a coupling end opposite the sensing end,
a sensing element disposed within the sensor housing,
a heating element disposed within the sensor housing, and
a tip cover removably coupled to the sensing end of the sensor housing;
visually inspecting the sensing assembly for physical damage;
in response to determining that the sensing assembly is not severely damaged, disassembling the sensing assembly;
replacing the tip cover of the sensing assembly with a new tip cover;
visually inspecting the sensor housing;
in response to determining based on the visual inspection that the sensor housing is not damaged, retaining the sensor housing;
inspecting the sensing element;
in response to determining based on the inspection that the sensing element is not damaged, retaining the sensing element;

inspecting the heating element;
in response to determining based on the inspection that heating element is not damaged, retaining the heating element; and
remanufacturing the sensing assembly.

16. The method of claim 15, further comprising:
in response to determining based on the visual inspection that the sensor housing is damaged, replacing the sensor housing with a new sensor housing,
wherein the new sensor housing is used in the remanufacturing of the sensor assembly.

17. The method of claim 16, wherein the sensor housing being damaged comprises mounting threads of the sensor housing being damaged and/or the sensor housing being bent, cracked or corroded.

18. The method of claim 15, further comprising:
in response to determining based on the inspection that the sensing element is damaged, replacing the sensing element with a new sensing element,
wherein the new sensing element is used in remanufacturing of the sensor assembly.

19. The method of claim 15, further comprising:
in response to determining based on the inspection that the heating element is damaged, replacing the heating element with a new heating element,
wherein the new heating element is used in remanufacturing of the sensor assembly.

20. The method of claim 15, wherein the sensing assembly also comprises a support structure for the sensing element, and wherein the method further comprises:
inspecting the support structure; and
in response to determining based on the inspection that the support structure is damaged, replacing the support structure with a new support structure,
wherein the new support structure is used in remanufacturing of the sensor assembly.

* * * * *